United States Patent [19]

Bell et al.

[11] Patent Number: 5,043,334
[45] Date of Patent: Aug. 27, 1991

[54] CEPHALOSPORIN ANTIBIOTICS

[75] Inventors: Richard Bell, South Ruislip; Michael W. Foxton, Chalfont St. Giles; Brian E. Looker, Greenford, all of England

[73] Assignee: Glaxo Group Limited, London, England

[21] Appl. No.: 441,612

[22] Filed: Nov. 27, 1989

Related U.S. Application Data

[63] Continuation of Ser. No. 250,604, Sep. 29, 1988, abandoned, which is a continuation of Ser. No. 793,900, Nov. 1, 1985, abandoned.

[30] Foreign Application Priority Data

| Nov. 2, 1984 | [GB] | United Kingdom | 8427807 |
| Nov. 2, 1984 | [GB] | United Kingdom | 8427808 |
| Nov. 2, 1984 | [GB] | United Kingdom | 8427809 |
| Sep. 4, 1985 | [GB] | United Kingdom | 8521975 |
| Sep. 4, 1985 | [GB] | United Kingdom | 8521976 |

[51] Int. Cl.$^5$ ............. C07D 501/20; A61K 31/545
[52] U.S. Cl. .................... 514/207; 540/222; 540/228
[58] Field of Search ........... 540/225, 221, 222, 228; 514/207

[56] References Cited

U.S. PATENT DOCUMENTS

| 4,278,793 | 7/1981  | Durckheimer et al. | 544/27  |
| 4,294,960 | 10/1981 | Takaya et al.      | 544/22  |
| 4,328,225 | 5/1982  | Vignau et al.      | 424/246 |
| 4,341,891 | 7/1982  | Gessell et al.     | 528/483 |
| 4,426,519 | 1/1984  | Vignau et al.      | 544/27  |
| 4,431,643 | 2/1984  | Takaya et al.      | 424/246 |
| 4,439,433 | 3/1984  | Heymes et al.      | 424/246 |
| 4,470,983 | 9/1984  | Blumbach et al.    | 424/246 |
| 4,550,102 | 10/1985 | Teraji et al.      | 514/206 |
| 4,614,819 | 9/1986  | Nagai et al.       | 540/222 |
| 4,785,090 | 11/1988 | Tsuruoka et al.    | 540/222 |
| 4,822,888 | 4/1989  | Takaya et al.      | 548/195 |

FOREIGN PATENT DOCUMENTS

| 111935   | 6/1984  | European Pat. Off. |
| 135142   | 3/1985  | European Pat. Off. |
| 2499995  | 8/1982  | France. |
| 58-167594 | 10/1983 | Japan. |
| 2025933  | 1/1980  | United Kingdom. |
| 2028305  | 3/1980  | United Kingdom. |
| 2031413  | 4/1980  | United Kingdom. |
| 2039890  | 8/1980  | United Kingdom. |

Primary Examiner—Nicholas S. Rizzo
Attorney, Agent, or Firm—Bacon & Thomas

[57] ABSTRACT

Compounds of general formula (I)

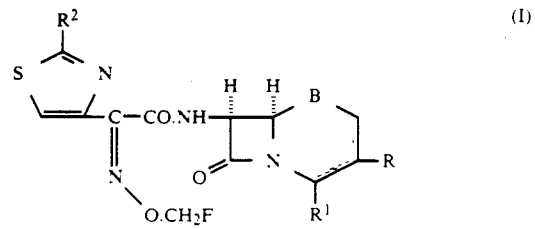

(where
$R^1$ is a carboxyl group, a group $COO^\ominus$ or a blocked carboxyl group;
$R^2$ is an amino or protected amino group; and
R is hydrogen or a group of the formula $CH_2X$, where X represents a halogen atom, a hydroxyl group, an acetoxy group; a group of the formula $O.CO.NHR^3$, where $R^3$ is hydrogen, a $C_{1-4}$ alkyl group optionally substituted by 1 to 3 halogen atoms or an N-protecting group; a group of the formula $OR^4$, where $R^4$ is a $C_{1-4}$ alkyl group optionally substituted by halogen or a $C_{1-4}$ alkoxy group; or a pyridinium, 3-carbamoyl-pyridinium or 4-carbamoyl-pyridinium group;
B is —S— or —SO— (α- or β-); and the dotted line bridging the 2-, 3- and 4- positions indicates that the compound is a ceph-2-em or ceph-3-em compound) and salts thereof, the compounds of formula (I) being associated with an anion when X represents a pyridinium, 3-carbamoylpyridinium group or a 4-carbamoylpyridinium group and $R^1$ is other than $COO^\ominus$) are disclosed.

Processes for their preparation and pharmaceutical compositions containing them are also disclosed.

3 Claims, No Drawings

CEPHALOSPORIN ANTIBIOTICS

This application is a continuation, of application Ser. No. 250,604, filed Sept. 29, 1988, which is a continuation of Ser. No. 793,900, filed Nov. 1, 1985, now abandoned.

This invention relates to improvements in or relating to cephalosporins. More particularly it relates to new cephalosporin compounds and derivatives thereof having valuable antibiotic activity.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both Gram-positive and Gram-negative microorganisms, and a significant amount of research has been directed to the development of various types of broad spectrum cephalosporin antibiotics.

Thus, for example, in our British Patent Specification No. 1399086, we describe a novel class of cephalosporin antibiotics containing a 7β-(α-etherified oxyimino)acylamido group, the oxyimino group having the syn configuration. This class of antibiotic compounds is characterised by high antibacterial activity against a range of Gram-positive and Gram-negative organisms coupled with particularly high stability to β-lactamases produced by various Gram-negative organisms.

The discovery of this class of compounds has stimulated further research in the same area in attempts to find compounds which have improved properties, for example against particular classes of organisms, especially Gram-negative organisms. This interest is reflected in the very large numbers of patent applications which have been filed relating to cephalosporin antibiotics having particular oxyimino etherifying groups in combination with particular substituents both on the 7β-acylamido side chain and at the 3-position of the cephalosporin nucleus.

In British Patent Specification No. 1604971 a wide variety of cephalosporin antibiotics are generically disclosed in which the 7β-position side-chain may be selected from, inter alia, a 2-(2-aminothiazol-b 4-yl)-2-(etherified oxyimino)acetamido group, in which the etherifying group, amongst very many possible meanings, may be an alkyl group (e.g. methyl substituted by a halogen atom, although there is no specific exemplification of compounds having such a group and the preferred etherifying group is stated to be an unsubstituted methyl group. Preferred halogen atoms are stated to be chlorine and bromine atoms. The 3-position group may also be selected from a very large number of alternatives and possible 3-substituents include alkoxymethyl, optionally substituted pyridiniummethyl, optionally substituted carbamoyloxymethyl, hydroxymethyl, acetoxymethyl, halomethyl, alkoxymethyl and hydrogen. British Patent Specification No. 1604971 describes cephalosporins having sulphur at the 1-position while British Patent Specification No. 1603212 describes related sulphoxides.

British Patent Specification No. 1576625 contains a generic definition of cephalosporin compounds having a 7β-(α-etherified oxyimino)acetamido side chain wherein the etherifying group is an aliphatic hydrocarbon group which may have suitable substituent(s) (although the "suitable substituent(s)" specifically mentioned for illustration do not include halogen atoms), which side chain is further o-substituted by a group which inter alia may be an aminothiazolyl group. The 3-position group may also be selected from a large number of alternatives and possible 3-substituents within the generic definition are hydroxymethyl, acetoxymethyl, halomethyl and optionally substituted carbamoyloxymethyl groups.

In British Patent Application No. 2039890A a wide variety of cephalosporin antibiotics are generically disclosed in which the 7β-position side chain is a 2-(2-aminothiazol-4-yl)-2-(etherified oxyimino)acetamido group. One possible etherifying group recited is a halo-lower-alkyl group (with a fluoromethyl group being mentioned inter alia as an illustration). According to the generic definition, the 3-position of the cephalosporin nucleus may inter alia be a carbamoyloxymethyl group. However, in the compounds specifically exemplified, only 2-bromoethyl, 2-chloroethyl and 2,2,2-trifluoroethyl groups are found as examples of halo-lower-alkyl groups.

In British Patent Application No. 2017702A the corresponding oxyimino etherifying group, according to the generic definition, may inter alia be a straight-chain $C_{1-4}$ alkyl group terminally monosubstituted e.g. by a halogen atom. The 3-position group of the cephalosporin nucleus may, according to the generic definition, inter alia be a carbamoyloxymethyl group. However, in the compounds specifically exemplified, only 2-bromoethyl and 2-iodoethyl groups are found as examples of haloalkyl groups.

European Patent Application No. 111935 generically defines cephalosporin compounds in which the 7β-position side chain may be selected from, inter alia, a 2-(2-aminothiazol-4-yl)-2-(etherified oxyimino)alia, acetamido group in which the etherifying group may be chosen from a large number of possibilities, including alkyl groups which may carry, inter alia, one or more halogen atoms. According to the generic definition, the 3-position group of the cephalosporin nucleus may inter alia be a carbamoyloxymethyl, acetoxymethyl or halomethyl group. These compounds have no stated antibiotic utility, being solely for use as intermediates in the synthesis of the final products which are restricted to 3-quinoliniummethyl and 3-isoquinoliniummethyl compounds. However, in the compounds specifically exemplified, only difluoromethyl and 2,2,2-trifluoroethyl groups are found as examples of haloalkyl oxime groups, and these are only present in combination with isoquinoliniummethyl and 4-methylquinoliniummethyl groups at the 3-position in the final products of the processes, and not in the intermediate cephalosporin compounds French Patent Specification No. 2499995 discloses cephalosporin antibiotics having a 2-(2-aminothiazol-4-yl)-2-(etherified oxyimino)acetamido 7β side-chain wherein the oxime etherifying group may be inter alia an optionally substituted $C_{1-6}$ alkyl group Possible substituents are said to include halogen such as chlorine, bromine or iodine, there being no specific mention of fluorine. There is specific exemplification only of bromoethyl as the etherifying group. The 3-substituent may be inter alia $C_{1-6}$ alkoxymethyl optionally interrupted by a heteroatom.

Japanese Patent Specification No. 58167594 describes cephalosporin antibiotics having in the 7β-position a 2-(2-aminothiazol-4-yl)-2-(etherified oxyimino)acetamido group in which the etherifying group is lower alkyl optionally substituted inter alia by fluorine but no compounds are specifically disclosed in which the etherifying group is a fluoromethyl group. The 3-substituent is lower alkyl or lower alkoxymethyl.

British Patent Specification No. 1600735 also discloses a large number of cephalosporin antibiotics including within its generic disclosure compounds in which the 7-substituent is a 2-(2-aminothiazol-4-yl)-2-(etherified oxyimino)acetamido group, the oxime etherifying group being defined inter alia as an aliphatic hydrocarbon residue which may be substituted by halogen. Fluoromethyl is mentioned as an example of an etherifying group but the specific exemplification illustrates only chloroethyl and 2,2,2-trifluoroethyl groups. The 3-substituent may be inter alia hydrogen.

We have now discovered that by the selection of a (Z)-2-(2-aminothiazol-4-yl)-2-(etherified oxyimino)acetamido group at the 7β-position in combination with hydrogen or certain specific groupings at the 3-position, and also by the selection of a monofluoromethoxyimino group as the etherified oxyimino grouping, cephalosporin compounds having a particularly advantageous profile of activity (described in more detail below) against a wide range of commonly encountered pathogenic organisms may be obtained.

According to the present invention, therefore we provide compounds of the general formula (I)

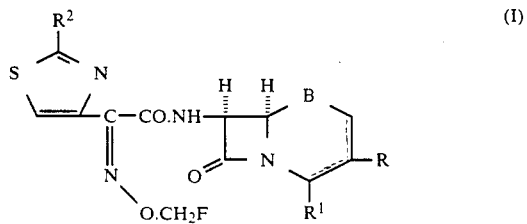

(where
  $R^1$ is a carboxyl group, a group COO or a blocked carboxyl group;
  $R^2$ is an amino or protected amino group;
  R is hydrogen or a group of the formula $CH_2X$, where
    X represents a halogen atom, a hydroxyl group, an acetoxy group; a group of the formula O.CO.NHR$^3$, where $R^3$ is hydrogen, a $C_{1-4}$ alkyl group optionally substituted by 1 to 3 halogen atoms or an N-protecting group; a group of the formula OR$^4$, where $R^4$ is a $C_{1-4}$ alkyl group optionally substituted by halogen or a $C_{1-4}$ alkoxy group; or a pyridinium, 3-carbamoylpyridinium or 4-carbamoyl-pyridinium group;
  B is —S— or —SO—(α- or β-); and the dotted line bridging the 2-, 3- and 4- positions indicates that the compound is a ceph-2-em or ceph-3-em compound) and salts thereof, the compound of formula (I) being associated with an anion when X represents a pyridinium, 3-carbamoylpyridinium group or 4-carbamoylpyridinium group and $R^1$ is other than COO$^\ominus$.

Where $R^1$ is a blocked carboxyl group the blocking group may, for example, be the residue of an ester-forming aliphatic or araliphatic alcohol or of an ester-forming phenol, silanol or stannanol (the said alochol, phenol, silanol or stannanol preferably containing from 1 to 20 carbon atoms)

Where $R^2$ is a protected amino group, the protecting group may be, for example, a trityl or acyl (for example chloroacetyl or formyl) group or the amino group may be protonated.

The compounds according to the invention are syn isomers. The syn isomeric form is defined by the configuration of the

—O.CH$_2$F group with respect to the carboxamido group In this specification, the syn configuration is denoted structurally as

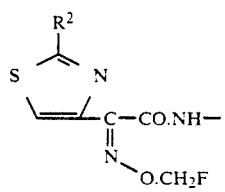

It will be understood that since the compounds according to the invention are geometric isomers, some admixture with the corresponding anti isomer may occur.

The compounds of formula (I) include both active antibiotics and intermediates for their preparation. This is set out in greater detail hereinafter.

It will be appreciated that salts of the compounds for use in medicine should be non-toxic. Similarly where $R^1$ is a carboxyl blocking group in compounds to be used in medicine, this should represent a metabolically labile non-toxic ester function.

Thus, antibiotically active compounds according to the invention may be represented by the general formula (Ia)

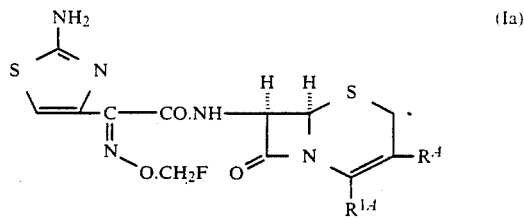

(wherein $R^A$ is hydrogen in RA is hydrogen, on acetoxymethyl group, a group of formula $CH_2O.CO.NHR^{3A}$ where $R^{3A}$ is hydrogen or a $C_{1-4}$ alkyl group optionally substituted by 1 to 3 halogen atoms; a group of the formula $CH_2OR^4$, where $R^4$ is as defined above; or a pyridiniummethyl, 3-carbamoylpyridiniummethyl or 4-carbamoylpyridiniummethyl group, and $R^{1A}$ is a carboxyl group or, when $R^A$ is a pyridiniummethyl, 3-carbamoylpyridiniummethyl or 4-carbamoylpyridiniummethyl group, a group COO$^-$, and the non-toxic salts and non-toxic metabolically labile esters thereof.

As indicated above certain of the compounds according to the invention may be used as starting materials for the preparation of other cephalosporins having antibiotic activity. In particular, compounds of formula (I) in which R is CH₂X where X is a leaving group such as a halogen atom or a hydroxy or acyloxy group may be used for preparing other cephalosporins possessing a syn 2-(2-aminothiazol-4-yl)-2-monofluoromethoxyiminoacetamido group at the 7β-position and a different substituent at the 3-position. This is set out in greater detail hereinafter.

The compounds of formula (Ia) according to the invention and their non-toxic salts and metabolically labile esters exhibit broad spectrum antibiotic activity both in vitro and in vivo. They have high activity against both Gram-positive and Gram-negative organisms, including many β-lactamase producing strains. The compounds also possess high stability to β-lactamases produced by a range of Gram-negative and Gram-positive organisms.

Compounds of formula Ia according to the invention have been found to exhibit high activity against strains (including penicillinase-producing strains) of Gram-positive bacteria such as *Staphylococcus aureus*, *Staphylococcus epidermidis* and Streptococcus species. This is coupled with high activity against various members of the Enterobacteriaceae (e.g. strains of *Escherichia coli*, *Klebsiella pneumoniae*, *Citrobacter diversus*, *Enterobacter cloacae*, *Serratia marcescens*, *Proteus mirabilis* and indole-positive Proteus organisms such as *Proteus vulqaris*, *Proteus morqanii* and Providence species) and strains of *Haemophilus influenzae* and *Acinetobacter calcoaceticus* as well as good activity against Pseudomonas species. This combination of high activity against Gram-positive organisms with high activity against Gram-negative organisms possessed by the compounds of the invention is unusual and particularly advantageous.

Compounds of formula Ia is which R is a pyridiniummethyl group have shown especially high activity against the above organisms, in particular against Enterobacter, Acinetobacter and Pseudomonas.

Non-toxic salt derivatives which may be formed by reaction of the carboxyl group present in the compounds of formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenylethylbenzylamine, dibenzylethylenediamine, ethanolamine, diethanolamine and N-methylglucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quaternary amino groups or sulphonic acid groups, or with a resin containing carboxyl groups, e.g. a polyacrylic acid resin. Soluble base salts (e.g. alkali metal salts such as the sodium salt) of the compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Non-toxic metabolically labile ester derivatives which may be formed by esterification of the carboxyl group in the parent compound of formula (I) include acyloxyalkyl esters, e.g. lower alkanoyloxy-methyl or -ethyl esters such as acetoxy-methyl or -ethyl or pivaloyloxymethyl esters. In addition to the above ester derivatives, the present invention includes within its scope the compounds of formula (I) in the form of other physiologically acceptable equivalents, i.e. physiologically acceptable compounds which, like the metabolically labile esters, are converted in vivo into the parent antibiotic compound of formula (I).

These and other salt and ester derivatives such as the salts with toluene-p-sulphonic and methanesulphonic acids or the esters with t-butyl or diphenylmethyl esterifying groups may be employed as intermediates in the preparation and/or purification of the present compounds of formula (I), for example in the processes described below.

It will be appreciated that the compounds of the invention wherein R is a pyridiniummethyl group, a 3-carbamoylpyridiniummethyl group or a 4-carbamoylpyridinium methyl group and wherein R¹ not a blocked carboxy group are usually present in the form of a betaine containing a positively-charged pyridinium group and a carboxylate group, and therefore esters and salts of compounds of formula (I) with bases will be associated with an anion to balance the positive charge on the pyridinium ring. Such an anion will also be non-toxic and may be derived from any of the acids described above which will form non-toxic salt derivatives.

The compounds of the invention may be used for treating a variety of diseases caused by pathogenic bacteria in human beings and animals, such as septicaemia, respiratory tract infections, skin and soft tissue infections and urinary tract infections.

According to another embodiment of the invention we provide a process for the preparation of compounds of general formula (I) as hereinbefore defined which comprises (A) acylating a compound of the formula (II)

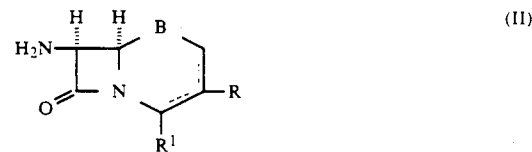

(wherein R, R¹, B and the dotted line are as defined above) which may be in the form of a salt, e.g. a betaine or an acid addition salt (the anion of which may be derived, for example, from a mineral acid such as hydrochloric, hydrobromic, sulphuric, nitric or phosphoric acid or an organic acid such as methanesulphonic or toluene-p-sulphonic acid) or an N-silyl derivative thereof, with an acid of formula (III)

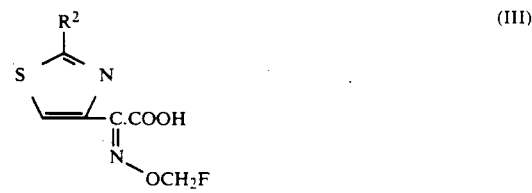

(wherein R² is as defined above) or a salt thereof or with an acylating derivative thereof;

or (B) to produce a compound of general formula (I) wherein R represents a group CH₂X, and wherein X represents a pyridinium, 3-carbamoylpyridinium or -carbamoylpyridinium group, reacting a compound of formula (IV)

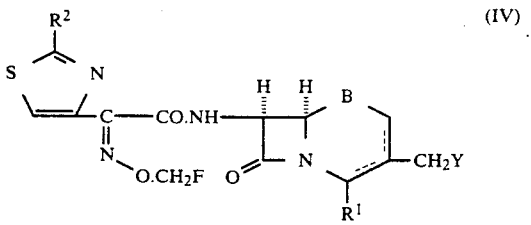

(wherein $R^1$, $R^2$, B and the dotted line are as hereinbefore defined; and Y is a replaceable residue of a nucleophile, e.g. an acetoxy or dichloroacetoxy group or a chlorine, bromine or iodine atom) or a salt thereof, with a pyridine compound of the formula (V)

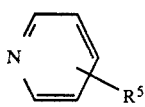

(wherein $R^5$ is hydrogen, a 3-carbamoyl group or a 4-carbamoyl group);

or (C) to produce a compound of general formula (I) wherein R represents a group —$CH_2X$, wherein X represents an acetoxy group or a group —$O.CO-NHR^3$ wherein $R^3$ is as hereinbefore defined, reacting a compound of general formula I wherein R is a hydroxymethyl group or a salt thereof with an acylating agent serving to convert said hydroxy group into an acetoxy group or a group —$O.CO.NHR^3$ as defined above;

or (D) to produce a compound of formula (I) where R is a group —$CH_2X$ where X is a group $OR^4$ as defined above, reacting a compound of general formula (I) as hereinbefore defined in which R is a hydroxymethyl group with an etherifying agent serving to convert said hydroxymethyl group into a group $CH_2OR^4$ where $R^4$ is as defined above;

or (E) to produce a compound of general formula (I) where R is a group —$CH_2X$ where X is a hydroxy group, 3-deacetylating a compound of general formula I where R is a group —$CH_2X$ where X is an acetoxy group or a salt thereof; whereafter, if necessary and/or desired in each instance, any of the following reactions, in any appropriate sequence, are carried out:

i) conversion of a $\Delta^2$-isomer into the desired $\Delta^3$-isomer,
ii) reduction of a compound wherein B is —SO— to form a compound wherein B is —S—,
iii) conversion of a carboxyl group into a non-toxic metabolically labile ester function,
iv) formation of a non-toxic salt function, and
v) removal of any carboxyl blocking and/or N-protecting groups.

The above reactions i) to v) may be carried out in conventional manner as indicated below.

In the above-described process (A), the starting material of formula (II) is preferably a compound wherein B is —S— and the dotted line represents a ceph-3-em compound.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Acylations employing acid halides may be effected in aqueous and non-aqueous reaction media, conveniently at temperatures of from $-50°$ to $+50°$ C., preferably $-40°$ to $+30°$ C., if desired in the presence of an acid binding agent. Suitable reaction media include aqueous ketones such as aqueous acetone, aqueous alcohols such as aqueous ethanol, esters such as ethyl acetate, ethers such as tetrahydrofuran, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-$\gamma$-dimethylaminopropylcarbodiimide; a carbonyl compound such as carbonyldiimidazole; an isoxazolium salt such as N-ethyl-5-phenylisoxazolium perchlorate; or N-ethoxycarbonyl-2-ethoxy-1,2-dihydroquinoline.

Acylation may also be effected with other amide-forming derivatives of acids of formula (III) such as, for example, an activated ester, a symmetrical anhydride or a mixed anhydride (e.g. formed with pivalic acid or with a haloformate, such as a lower alkylhaloformate). Mixed anhydrides may also be formed with phosphorus acids (for example phosphoric or phosphorous acids), sulphuric acid or aliphatic or aromatic sulphonic acids (for example toluene-p-sulphonic acid). An activated ester may conveniently be formed in situ using, for example, 1-hydroxybenzotriazole in the presence of a condensing agent as set out above. Alternatively, the activated ester may be preformed.

Acylation reactions involving the free acids or their above-mentioned amide-forming derivatives are desirably effected in an anhydrous reaction medium, e.g. methylene chloride, tetrahydrofuran, dimethylformamide or acetonitrile.

An alternative method of activation is, for example, by reacting an acid of formula (III) with a solution or suspension preformed by adding a carbonyl halide, in particular oxalyl chloride or phosgene, or a phosphoryl halide such as phosphorus oxychloride to a solvent such as a halogenated hydrocarbon, for example methylene chloride, containing a lower acyl tertiary amide such as N,N-dimethylformamide. The activated form of the the acid of formula (III) may then be reacted with a 7-amino compound of formula (II) in a suitable solvent or mixture of solvents for example an alkanol such as an alkanol, e.g. ethanol or methanol; halogenated hydrocarbons, e.g. dichloromethane; esters, e.g. ethyl acetate; ethers, e.g. dioxan or tetrahydrofuran; ketones, e.g. acetone; amides, e.g. dimethylacetamide; acetonitrile; water; and mixtures thereof. The acylation reaction may conveniently be effected at temperatures of from $-50°$ to $+50°$ C., preferably $-40°$ to $+30°$ C., if desired in the presence of an acid binding agent, for example as described above (e.g. triethylamine, dimethylaniline or sodium bicarbonate).

If desired, the above acylation reactions may be carried out in the presence of a catalyst such as 4-dimethylaminopyridine.

The acids of formula (III) and acylating agents corresponding thereto may, if desired, be prepared and employed in the form of their acid addition salts. Thus, for example, acid chlorides may conveniently be employed as their hydrochloride salts, and acid bromides as their hydrobromide salts.

In reaction (B) a pyridine compound of formula (V) may act as a nucleophile to displace a wide variety of substituents Y from a cephalosporin of formula (IV). To some extent the facility of the displacement is related to the pKa of the acid HY from which the substituent is derived. Thus atoms or groups Y derived from strong acids tend, in general, to be more easily displaced than atoms or groups derived from weaker acids. The facility of the displacement is also related, to some extent, to the precise character of the substituent $R^5$ in the compound of formula (V).

The displacement of Y by the pyridine compound of formula (V) may conveniently be effected by maintaining the reactants in solution or suspension. The reaction is advantageously effected using from 1 to 10 moles of the pyridine compound.

Nucleophilic displacement reactions may conveniently be carried out on those compounds of formula (IV) wherein the substituent Y is a halogen atom or an acyloxy group, for example as discussed below.

Acyloxy groups

Compounds of formula (IV) wherein Y is an acetoxy group are convenient starting materials for use in the nucleophilic displacement reaction with the pyridine compound of formula (V). Alternative starting materials in this class include compounds of formula (IV) in which Y is the residue of a substituted acetic acid e.g. chloroacetic acid, dichloroacetic acid and trifluoroacetic acid.

Displacement reactions on compounds (IV) possessing Y substituents of this class, particularly in the case where Y is an acetoxy group, may be facilitated by the presence in the reaction medium of iodide or thiocyanate ions. Reactions of this type are described in more detail in British Patent Specifications Nos. 1132621 and 1171603.

The substituent Y may also be derived from formic acid, a haloformic acid such as chloroformic acid, or a carbamic acid.

When using a compound of formula (IV) in which Y represents an acetoxy or substituted acetoxy group, it is generally desirable that the group $R^3$ in formula (IV) should be a hydrogen atom and that B should represent —S—. In this case, the reaction is advantageously effected in an aqueous medium, preferably at a pH of 5 to 8, particularly 5.5 to 7.

The above-described process employing compounds of formula (IV) in which Y is the residue of a substituted acetic acid may be carried out as described in British Patent Specification No. 1241657.

When using compounds of formula (IV) in which Y is an acetoxy group, the reaction is conveniently effected at a temperature of 30° C. to 110° C., preferably 50° to 80° C.

Halogens

Compounds of formula (IV) in which Y is a chlorine, bromine or iodine atom can also be conveniently used as starting materials in the nucleophilic displacement reaction with the pyridine compound of formula (V). When using compounds of formula (IV) in this class, B may represent —SO— and $R^3$ may represent a carboxyl blocking group. The reaction is conveniently effected in a non-aqueous medium which preferably comprises one or more organic solvents, advantageously of a polar nature such as ethers, e.g. dioxan or tetrahydrofuran; halogenated hydrocarbons, e.g. dichloromethane, esters, e.g. ethyl acetate; amides, e.g. formamide and N,N-dimethylformamide; and ketones e.g. acetone. In certain cases the pyridine compound itself may be the solvent. Other suitable organic solvents are described in more detail in British Patent Specification No. 1326531. The reaction medium should be neither extremely acidic nor extremely basic. In the case of reactions carried out on compounds of formula (IV) in which $R^1$ is a blocked carboxyl group the 3-pyridiniummethyl product will be formed as the corresponding halide salt which may, if desired, be subjected to one or more ion exchange reactions to obtain a salt having the desired anion.

When using compounds of formula (IV) in which Y is a halogen atom as described above, the reaction is conveniently effected at a temperature of −10° to +50°, preferably +10° to +30° C.

Carbamoylation of 3-hydroxymethyl compounds of formula (IV) in Process C may be effected by conventional methods using suitable acylating (i.e. carbamoylating) agents. Suitable carbamoylating agents include isocyanates of formula $R^3$.NCO (wherein $R^3$ is as defined above) to give a compound containing a 3-position substituent having the formula —CH$_2$O.CONHR$^3$ (wherein $R^3$ has the above defined meaning). The carbamoylation reaction may desirably be effected in the presence of a solvent or solvent mixture selected from hydrocarbons (e.g. aromatic hydrocarbons such as benzene and toluene), halogenated hydrocarbons (e.g. dichloromethane), amides (e.g. formamide or dimethylformamide), esters (e.g. ethyl acetate), ethers (e.g. cyclic ethers such as tetrahydrofuran and dioxan), ketones (e.g. acetone), sulphoxides (e.g. dimethylsulphoxide) and mixtures of these solvents. The reaction may conveniently be carried out at a temperature of between −80° C. and the boiling temperature of the reaction mixture, for example up to 100° C., preferably between −20° and +30° C.. Where the group $R^3$ is an N-protecting group it may subsequently be cleaved, e.g. by hydrolysis, to form a 3-carbamoyloxymethyl group. Examples of N-protecting groups $R^3$ which are readily cleavable upon subsequent treatment include acyl groups, especially lower alkanoyl group such as acetyl, halo-substituted lower alkanoyl groups such as mono-, di- or trichloroacetyl, chlorosulphonyl or bromosulphonyl or halogenated alkoxycarbonyl groups such as 2,2,2-trichloroethoxycarbonyl. Such N-protecting groups may generally be cleaved by acid or base catalysed hydrolysis (e.g. by base catalysed hydrolysis using sodium bicarbonate). Halogenated groups such as chlorosulphonyl, dichlorophosphoryl, trichloroacetyl and 2,2,2-trichloroethoxycarbonyl may also be cleaved reductively, while groups such as chloroacetyl may also be cleaved by treatment with thioamides such as thiourea.

The carbamoylating agent is desirably used in excess (for example at least 1.1 moles relative to the compound of formula (IV)). The carbamoylation may be assisted by the presence of base, e.g. a tertiary organic base such as a tri-(lower alkyl)amine (e.g. triethylamine) or by employing the compound (IV) in the form of an alkali metal (e.g. sodium) salt, although such assistance may not be necessary in the case of more active isocyanates, e.g. compounds when $R^3$ is a strongly electron-withdrawing group such as chlorosulphonyl or trichloroacetyl. Carbamoylations involving reaction of a free acid of formula (IV) with excess isocyanate wherein $R^3$ is a group such as chlorosulphonyl or trichloroacetyl are thus of particular practical advantage by virtue of the simplicity of the reaction conditions, since there is no need for temporary blocking and subsequent deblocking of the 4-position carboxy group of the cephalosporin and since the electron-withdrawing $R^3$ group in the resulting N-protected 3-carbamoyloxymethyl cephalosporin product is readily removed by, for example, hydrolysis with aqueous sodium bicarbonate.

It should be noted that it may be convenient to retain or even introduce an N-substituting group $R^3$ during transformations of intermediate 3-carbamoyloxymethyl compounds in order to minimise unwanted side reactions involving the carbamoyloxymethyl group.

Another useful carbamoylating agent is cyanic acid, which is conveniently generated in situ, for example, from an alkali metal cyanate such as sodium cyanate, the reaction being facilitated by the presence of an acid, e.g. a strong organic acid such as trifluoroacetic acid. Cyanic acid effectively corresponds to the isocyanate compounds mentioned above wherein $R^3$ is hydrogen and therefore converts compounds of formula (IV) directly into their 3-carbamoyloxymethyl analogues.

Alternatively, carbamoylation may be effected by reaction of the compound of formula (IV) with phosgene or carbonyldiimidazole followed by ammonia or the appropriate substituted amine, optionally in an aqueous or non-aqueous reaction medium.

Acylation of 3-hydroxymethyl compounds according to process (C) may be effected by conventional methods, for instance in an analogous manner to that described in British Patent Specification No. 1141293, i.e. by blocking the 4-carboxy group (where this is not already blocked), acetylating the 3-hydroxymethyl group of the protected compound and, if desired, subsequently removing the blocking group.

In process (D) above a wide variety of substituents $CH_2X$ may serve as the group which may be converted into the group $CH_2OR^4$. General methods suitable for the preparation of the ethers are discussed by Meerwein in "Methoden der Organischen Chemie" edited by Müller, Georg Thieme Verlag, Stuttgart, 1965, Vol. VI(3) pp 7–137 and in "The Chemistry of the Ether Linkage" edited by Patai, Interscience, London, 1967, especially at pp. 445–498 where methods involving the action of $H^+$, $OH^-$, Grignard reagents and peracids are discussed. Other methods involving the use of isoureas are discussed by Dabritz, *Angew. Chem.* 1966, 5, 470 and Vowinkel, *Chem. Ber.* 1967, 100, 16 and methods involving the use of alkyl phosphites are discussed by Chopard, *H.C.A;* 1967, 50, 1021 and Harvey, *Tetrahedron,* 1966, 22, 2561.

Thus for example etherification may be carried out by reaction of the appropriate 3-hydroxymethyl compound with a diazo compound, e.g. a lower diazoalkane such as, for example, diazomethane, having first protected the 4-carboxyl group. With diazo reagents it is desirable to use mild conditions. The rate of reaction of the diazo compound may be accelerated by the addition of a Lewis acid, e.g. boron trifluoride or aluminium trichloride. Reaction with diazo compounds may be effected in organic solvents such as halogenated hydrocarbons, e.g. dichloromethane or carbon tetrachloride, an ether, e.g. diethyl ether, tetrahydrofuran or dioxan, esters, e.g. ethyl acetate or light petroleum fractions and the reaction may be effected at $-15°$ to $+50°$ C. preferably at about 5° C. The etherification may also be carried out, for example, by reaction of the appropriate 3-halomethyl compound, for example the appropriate 3-bromomethyl sulphoxide, with the appropriate alcohol in the presence of a mercuric (II) salt such as mercuric perchlorate or, more conveniently, mercuric trifluoroacetate. The alcohol is conveniently used alone as the reaction solvent or may be used together with other solvents such as halogenated hydrocarbons, e.g. dichloromethane; ethers, e.g. dioxan; nitriles, e.g. acetonitrile; and sulphoxides, e.g. dimethylsulphoxide. The reaction may be effected at a temperature in the range of from $-20°$ to $+100°$ C., conveniently from 0° to 40° C. Other methods which may be applied for use in process (B) above include, for example, those described in British Patent Specification No. 2110688, Japanese Patent Specification No. 57192392 and J. Chem. Soc. Perkin I, 1983, pp2281-2286.

Compounds according to the invention in which X represents a hydroxyl group can be prepared by deacetylation of the corresponding 3-acetoxymethyl compounds according to process (E), for example by hydrolysis of the 3-acetoxymethyl compounds, e.g. as described for example in British Patent Specifications Nos. 1474519 and 1531212. A particularly convenient method for the deacetylation of a 3-acetoxymethyl compound is by the enzymatic hydrolysis described in our British Patent Specification No. 1,531,212 e.g. using an esterase derived from *Rhodosporidium toruloides.*

In any of the foregoing reactions, the reaction product may be separated from the reaction mixture, which may contain, for example, unchanged cephalosporin starting material and other substances, by a variety of processes including recrystallisation, ionophoresis, column chromatography and use of ion-exchangers (for example by chromatography on ion-exchange resins) or macroreticular resins.

A $\Delta^2$-cephalosporin ester derivative obtained in accordance with the process of the invention may be converted into the corresponding desired $\Delta^3$-derivative by, for example, treatment of the $\Delta^2$-ester with a base, such as pyridine or triethylamine.

A ceph-2-em reaction product may also be oxidised to yield the corresponding ceph-3-em 1-oxide, for example by reaction with a peracid, e.g. peracetic or m-chloroperbenzoic acid; the resulting sulphoxide may subsequently be reduced as described hereinafter to yield the corresponding desired ceph-3-em sulphide.

Where a compound is obtained in which B is —SO— this may be converted into the corresponding sulphide by, for example, reduction of the corresponding acyloxysulphonium or alkoxysulphonium salt prepared in site by reaction the case of an acetoxysulphonium salt, reduction being effected by, for example, sodium dithionite or by iodide ion as in a solution of potassium iodide in a solvent e.g. acetic acid, acetone, tetrahydrofuran, dioxan, dimethylformamide or dimethylacetamide. The reaction may be effected at a temperature of from $-20°$ to $+50°$ C.

Metabolically labile ester derivatives of the compounds of formula (I) may be prepared by reacting a compound of formula (I) or a salt or protected derivative thereof with the appropriate esterifying agent such as an acyloxyalkyl halide (e.g. iodide) conveniently in an inert organic solvent such as dimethylformamide or acetone, followed, where necessary, by removal of any protecting groups.

Base salts of the compounds of formula (I) may be formed by reacting an acid of formula (I) with an appropriate base. Thus, for example, sodium or potassium salts may be prepared using the respective 2-ethylhexanoate or hydrogen carbonate salt. Acid addition salts may be prepared by reacting a compound of formula (I) or a metabolically labile ester derivative thereof with the appropriate acid.

Where a compound of formula (I) is obtained as a mixture of isomers, the syn isomer may be obtained by, for example, conventional methods such as crystallisation or chromatography.

For use as starting materials for the preparation of compounds of general formula (I) according to the invention, compounds of general formula (III) and acid halides and anhydrides corresponding thereto in their syn isomeric form or in the form of mixtures of the syn isomers and the corresponding anti isomers containing at least 90% of the syn isomer are preferably used.

The starting materials of formula (II) may also be prepared in conventional manner, for example, by nucleophilic displacement of the corresponding 3-acetoxymethyl compound with the appropriate nucleophile, e.g. as described in British Patent Specification No. 1028563, or by the method described in British Patent Specification No. 2052490A.

A further method for the preparation of the starting materials of formula (II) comprises deprotecting a corresponding protected 7β-amino compound in conventional manner, e.g. using $PCl_5$.

Where R in formula (II) is a group $CH_2X$ where X is a chlorine, bromine or iodine atom, ceph-3-em starting compounds may be prepared in conventional manner, e.g. by halogenation of a 7β-protected amino-3-methyl-ceph-3-em-4-carboxylic acid ester 1β-oxide and removal of the 7β-protecting group. After acylation of the resulting 7β-amino compound to form the desired 7β-acylamido group in process (A) above, the 1β-oxide group may subsequently be reduced. This is described in British Patent No. 1326531. The corresponding ceph-2-em compounds may be prepared by the method of Dutch published Patent Application No. 6902013 by reaction of a 3-methylceph-2-em compound with N-bromosuccinimide to yield the corresponding 3-bromomethylceph-2-em-compound.

The starting materials of formula (II) in which R is a hydroxymethyl group may be prepared, for example, by deacetylation of the corresponding 3-acetoxymethyl compound as described in British Patent Specifications Nos. 1474519 and 1531212.

Compounds of formula (II) may also be prepared by the method of British Patent Specification No. 1600735.

Acids of formula (III) and their derivatives are themselves novel compounds and form a further feature of the present invention. They may be prepared by etherification of a compound of formula (VI)

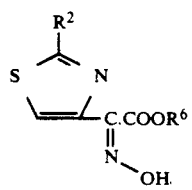

(VI)

(wherein $R^2$ is as hereinbefore defined and $R^6$ represents hydrogen or a carboxyl blocking group) or a salt thereof, by selective reaction with a compound of general formula (VII)

$$T.CH_2F \qquad (VII)$$

(wherein T is chloro, bromo or iodo), followed by removal of any carboxyl blocking group $R^6$. Separation of isomers may be effected either before or after such etherification. The etherification reaction is conveniently carried out in the presence of a base, e.g. potassium carbonate or sodium hydride, and is preferably conducted in an organic solvent, for example dimethylsulphoxide, a cyclic ether such as tetrahydro-furan or dioxan, or an N,N-disubstituted amide such as dimethylformamide. Under these conditions the configuration of the oxyimino group is substantially unchanged by the etherification reaction. When the compound of formula (VII) is employed in the form of a free acid or a salt with a base, the etherification reaction is generally carried out in the presence of a strong base, e.g., potassium t-butoxide, sufficient base being added to form a dianion. Furthermore, the reaction should be effected in the presence of a base if an acid addition salt of a compound of formula (VI) is used, the amount of base being sufficient to neutralise rapidly the acid in question.

Acids of formula (III) may also be prepared by reaction of a compound of formula (VIII)

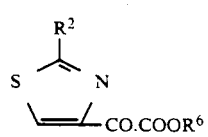

(VIII)

(wherein $R^2$ and $R^6$ are as hereinbefore defined) with a compound of formula (IX)

$$H_2N.O.CH_2F \qquad (IX)$$

followed by removal of any carboxyl blocking group $R^6$, and where necessary the separation of syn and anti isomers.

The acids of formula (III) may be converted into the corresponding acid halides and anhydrides and acid addition salts by conventional methods, for example as described hereinabove.

The starting materials of formula (IV) (where these are not compounds of formula (I) which may be prepared by methods A to E above) may be prepared by acylating the corresponding 7-amino compounds analogously to process (A) above.

Compounds of formula (IV) in which Y represents acyloxy groups other than acetoxy can be prepared by acylation of the corresponding 3-hydroxymethyl compounds which may be prepared for example by hydrolysis of the appropriate 3-acetoxymethyl compounds, e.g. as described in British Patent Specifications Nos. 1474519 and 1531212.

Other compounds of formula (IV) may be obtained from the 3-hydroxymethyl compound by conventional conversion reactions e.g. acylation or halogenation.

It should be appreciated that in some of the above transformations it may be necessary to protect any sensitive groups in the molecule of the compound in question to avoid undesirable side reactions. Examples of suitable protecting groups are given in "Protective Groups in Organic Synthesis" by Theodora W. Greene (John Wiley and Sons, 1981). For example, during any of the reaction sequences referred to above it may be necessary to protect the $NH_2$ group of the aminothiazolyl moiety, for example by tritylation, acylation (e.g. chloroacetylation or formylation), protonation or other conventional method. The protecting group may thereafter be removed in any convenient way which does not cause breakdown of the desired compound, e.g. in the case of a trityl group by using an optionally halogenated carboxylic acid, e.g. acetic acid, formic acid, chloroacetic acid or trifluoroacetic acid or using a mineral acid, e.g. hydrochloric acid or mixtures of such acids, preferably in the presence of a protic solvent such as water, or, in the case of a chloroacetyl group, by treatment with thiourea.

Carboxyl blocking groups used in the preparation of compounds of formula (I) or in the preparation of necessary starting materials are desirably groups which may readily be split off at a suitable stage in the reaction sequence, conveniently at the last stage. It may, however, be convenient in some instances to employ non-toxic metabolically labile carboxyl blocking groups such as acyloxy-methyl or -ethyl groups (e.g. acetoxymethyl or-ethyl or pivaloyloxymethyl) and retain these in the final product to give an appropriate ester derivative of a compound of formula (I).

Suitable carboxyl blocking groups are well known in the art, a list of representative blocked carboxyl groups being included in British Patent No. 1399086. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid catalysed hydrolysis or reduction is applicable in many cases, as is enzymically-catalysed hydrolysis.

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may, for example, be formulated for injection and may be presented in unit dose form, in ampoules, or in multi-dose containers, if necessary with an added preservative. The compositions may also take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

If desired, such powder formulations may contain an appropriate non-toxic base in order to improve the water-solubility of the active ingredient and/or to ensure that when the powder is reconstituted with water, the pH of the resulting aqueous formulation is physiologically acceptable. Alternatively the base may be present in the water with which the powder is reconstituted. The base may be, for example, an inorganic base such as sodium carbonate, sodium bicarbonate or sodium acetate, or an organic base such as lysine or lysine acetate. The antibiotic compounds may also, be formulated as suppositories e.g. containing conventional suppository bases such as cocoa butter or other glycerides.

Compositions for veterinary medicine may, for example, be formulated as intramammary preparations in either long acting or quick-release bases.

The compositions may contain from 0.1% upwards, e.g. 0.1–99% of the active material, depending on the method of administration. When the compositions comprise dosage units, each unit will preferably contain 100–3000 mg of the active ingredient e.g. 200–2000 mg. The daily dosage for adult human treatment will preferably range from 200 to 12000 mg e.g. 1000–9000 mg per day, depending inter alia on the nature of the infection and the route and frequency of administration. In general, intravenous or intramuscular administration will be employed, for example using 400 to 6000 mg,e.g. 500 to 4000 mg,per day of the active ingredient in adult human treatment. In treating Pseudomonas infections higher daily doses may be required. It will be appreciated that in some circumstances, for example, in the treatment of neonates, smaller dosage units and daily dosages may be desirable.

The antibiotic compounds according to the invention may be administered in combination with other therapeutic agents such as antibiotics, for example penicillins or other cephalosporins.

The following Examples and Preparations illustrate the invention. All temperatures are in ° C.; DMSO is dimethylsulphoxide; EtOH is ethanol; DMF is N,N-dimethylformamide. Kieselgel 60 is silica gel manufactured by E. Merck and Co. of Darmstadt, West Germany; Sorbsil U30 is silica gel manufactured by Joseph Crosfield and Son of Warrington, Cheshire, England. (Kieselgel and Sorbsil are registered Trade Marks).

Intermediate 1

Ethyl (Z)-2-fluoromethoxyimino-2-(2-triphenylmethylaminothiazol-4-yl)acetate

Ethyl (Z)-2-hydroxyimino-2-(2-triphenylmethylaminothiazol-4-yl)acetate, hydrochloride salt (8.7 g) was stirred with potassium carbonate (15.35 g) in dimethyl sulphoxide (30 ml) under nitrogen at 21°. Bromofluoromethane (ca 3 g) was added. The nitrogen flow was stopped and the stirring continued for two hours. The mixture was poured into an ice-water mixture with stirring and the solid was collected by filtration and washed with water. The solid was dissolved in methylene chloride and the organic layer was separated and dried with magnesium sulphate. Evaporation gave a foam. This was dissolved in methylene chloride and pre-absorbed onto Kieselgel 60 (50 g). This was added to the top of a column of similar silica (125 g) set up in 10% ethyl acetate in cyclohexane. The column was eluted successively with 10%, 20% and 33% ethyl acetate in cyclohexane. After combination of appropriate fractions, evaporation gave the title compound (8.06 g) as a foam; $\lambda_{max}$ (EtOH) 302 nm ($E_{1\,cm}^{1\%}$ 92), $\lambda_{infl}$ include 227.5 nm ($E_{1\,cm}^{1\%}$ 546) and 259 nm ($E_{1\,cm}^{1\%}$ 221), $\nu_{max}$ (CHBr$_3$) 3400 (NH), 1739 (ester) and 1533 cm$^{-1}$ (C=N).

INTERMEDIATE 2

(Z)-2-Fluoromethoxyimino-2-(2-triphenylme-thylaminothiazol-4-yl)acetic acid.

Intermediate 1 (7.8 g) was stirred under reflux with sodium hydroxide (0.83 g) in ethanol (50 ml) and water (10 ml) for 15 minutes. The mixture was cooled and the crystalline precipitate was collected by filtration and washed with ethanol and ether and dried. This solid was partitioned between methylene chloride (80 ml) and water (40 ml) with vigorous stirring and 88% orthophosphoric acid (2 ml) was added. Solid remained and this was collected by filtration. This solid was suspended in tetrahydrofuran (75 ml) and 2M hydrochloric acid (8 ml) was added when a solution formed. Evaporation reduced the volume of solution by one half and methylene chloride (50 ml) was added. The aqueous layer was extracted with more methylene chloride and the combined organic layers were washed with water, dried with magnesium sulphate and evaporated to a solid, the title compound (4.82 g); $\lambda_{infl}$ include 224nm ($D_{1\,cm}^{1\%}$ 564), 254.5 nm ($E_{1\,cm}^{1\%}$ 213) and 260 nm ($E_{1\,cm}^{1\%}$ 205); $\tau$(d$_6$DMSO) 1.02 (s; NH), 2.64 (s; phenyl protons) 2.91 (s; thiazole 5-H), and 4.29 (d, J 56Hz; CH$_2$F).

EXAMPLE 1 a)
(6R,7R)-7-[(Z)-2-fluoromethoxyimino-2-(2-triphenyl-methyl-aminothiazol-4-yl)acetamido]-3-(1-pyridinium-methyl)ceph-3-em-4-carboxylate Oxalyl chloride(0.37 ml) was added to a solution of N,N-dimethylformamide (0.38 ml) in methylene chloride (10 ml) at $-20°$ with stirring under nitrogen and the mixture was stirred with ice-water cooling for ten minutes. The mixture was recooled to $-20°$ and Intermediate 2 (1.85 g) was added. The solution was stirred with ice-water cooling for ten minutes before recooling to $-20°$. The solution was added to a solution of (6R,7R)-7-amino-3-(1-pyridiniummethyl)ceph-3-em-4-carboxylate, dihydrochloride, dihydrate, (1.52 g) in industrial methylated spirits (12 ml) and water (3 ml) containing triethylamine (2.35 ml) at ca $-10°$. The solution was allowed to warm to 21°. Water (50 ml) was added and the precipitate was collected by filtration, washed with water and methylene chloride and dried to give the title compound (1.24 g). $[\alpha]_D^{21}$ $-56.3°$ (c 1.01, DMSO), $\lambda_{max}$ (EtOH) 256.5nm ($E_{1\,cm}^{1\%}$ 239), $\lambda_{infl}$ include 225 nm ($E_{1\,cm}^{1\%}$ 436) and 262 nm ($E_{1\,cm}^{1\%}$ 225).

b)
(6R,7R)-7-[(Z)-2-(2-Aminothiazol-4-yl)-2-fluorome-thoxyiminoacetamido]-3-(1-pyridiniummethyl)ceph-3-em-4-carboxvlate The product of stage a) (1.12 g) was dissolved in formic acid (6 ml) with stirring at 21° and water (3 ml) was added. After 1.5 hours, the mixture was filtered and the filter-cake was leached with 30% water in formic acid. The combined filtrates were evaporated and the residue was triturated with acetone. The precipitate was collected by filtration, washed with acetone and dried to give the title compound (630 mg). $[\alpha]_D^{21}$ $-79.34°$ (c 0.31, DMSO), $\lambda_{max}$ 226.5 nm ($D_{1\,cm}^{1\%}$ 379), 256 nm ($E_{1\,cm}^{1\%}$ 366); $\lambda_{infl}$ 296 nm ($E_{1\,cm}^{1\%}$ 128).

EXAMPLE 2

(6R,7R)-7[(Z)-2-(2-Aminothiazol-4-yl)-2-fluoromethox-yiminoacetamido]-3-(1-pyridiniumethyl)ceph-3-em-4-carboxylate, bis hydrochloride (6R,7R)-7-[(Z)-2-(2-Tritylaminothiazol-4-yl)-2-fluoromethoxyiminoacetamido]-3-(1-pyridiniumethyl)-ceph-3-em-4-carboxylate (27 g) was stirred in formic acid (108 ml) for 5 minutes. Water (27 ml) was added and the mixture stirred at 22° to 25° during 2½ hours. Dichloromethane (135 ml) was added and the two-phase solution was stirred for 3 minutes. The upper aqueous phase was separated and concentrated hydrochloric acid (8.1 ml) added. The solution was washed with isopropyl ether (135 ml and 100 ml). The second isopropyl ether wash was extracted with water (2 ml). The aqueous extracts were combined and acetone (230 ml) added to the stirred solution during 1.25 hours. The mixture was stirred at ambient temperature for half an hour. The solid was collected by filtration, under nitrogen, and washed with acetone (2×50 ml). The solid was dried in vacuo at 40° for 18 hours to give 16.1 g of the title compound. $\nu_{max}$ (Nujol) includes 3200 (N—H); 1778 ($\beta$-lactam carbonyl), 1720 (CO$_2$H) and 1668+1558 (—CONH) cm$^{-1}$. $\tau$ values (DMSO-d$_6$) include 0.82, 1.30 and 1.75 (pyridinium ring protons); 2.94 (aminothiazole H); 4.10 (C-7 H); 4.26 (—O—CH$_2$F; $J_{HF}$=56 Hz); 4.32 (ABq, collapsed, —CH$_2$—N$^\oplus$); 6.32+6.51 (C-2 methylene, ABq, 18 Hz).

EXAMPLE 3 a) Diphenylmethyl (6R,7R)-3-carbamoyloxymethyl-7-[(Z)-2-fluorome-thoxyimino-2-(2-triphenylmethyl aminothiazol-4-yl)acetamido]ceph-3-em-4-carboxylate Oxalyl chloride (0.37 ml) was added to a solution of N,N-dimethylformamide (0.38 ml) in methylene chloride (10 ml) at $-20°$ with stirring under nitrogen and the mixture was stirred with ice-water cooling for ten minutes. The mixture was recooled to $-20°$ and Intermediate 2 (1.85 g) was added. The solution was stirred with ice-water cooling for ten minutes before recooling to $-20°$. A slurry of diphenylmethyl (6R,7R)-7-amino-3-carbamoyloxymethylceph-3-em-4-carboxylate (1.76 g) in methylene chloride (10 ml) containing N,N-dimethylaniline (1.26 ml) was added and the solution was allowed to warm to 21° over 30 minutes. The solution was washed with dilute hydrochloric acid and water twice, each time back-extracting with methylene chloride. The combined organic solutions were dried with magnesium sulphate and evaporated to dryness. The residue was redissolved in methylene chloride and filtered through Sorbsil U30 (100 g) in ethyl acetate 10 to 60% in petroleum ether (bpt 40°-60°). Combination of appropriate fractions and evaporation gave the title compound (1.89 g) as a foam; $[\alpha]_D^{21}$ +10.97° (c 1.09, chloroform), $\nu_{max}$(CHBr$_3$) 3400 (NH), 1789 ($\beta$-lactam), 1729 (ester and carbamate) and 1690 and 1520 cm$^{-1}$ (amide).

b)
(6R,7R)-3-Carbamoyloxymethyl-7-[(Z)-2-(2-amino-thiazol-4-yl)-2-fluoromethoxyiminoacetamido]ceph-3-em-4-carboxylic acid trifluoroacetate salt The product of stage a) (1.79 g) was dissolved in anisole (4 ml) and trifluoroacetic acid (16 ml) was added. After 55 minutes at 21°, water (2 ml) was added. After a further five minutes, the solution was diluted with diisopropyl ether (200 ml) and the precipitate was collected by filtration, washed with diisopropyl ether and dried to give the title compound (890 mg); $[\alpha]_D^{21}$ +43.15° (c 1.12, DMSO), $\nu_{max}$ (Nujol) 3700–2300 (NH$_2$, NH, OH and $\oplus$NH), 1775 ($\beta$-lactam), 1705 (COOH) and 1670 and 1545 cm$^{-1}$ (amide).

EXAMPLE 4 a) t-Butyl (6R,7R)-3-acetoxymethyl-7-[(Z)-2-fluoromethoxyimino-2-(2-triphenylmethylaminothiazol-4-yl)acetamido]-ceph-3-em 4-carboxylate The title compound (2.41 g) was prepared as a foam according to the method of Example 3a) from t-butyl 7-aminocephalosporanate (1.65 g) and exhibited $[\alpha]_D^{21}$ +21.0° (c 2.12, chloroform) $\nu_{max}$ (CHBr$_3$) 3395 (NH), 1789 ($\beta$-lactam) 1728 (esters) and 1692 and 1518 cm$^{-1}$ (amide).

b) (6R,7R)-3-Acetoxymethyl-7-[(Z)-2-(2-aminothiazol-4-yl)-2-fluoromethoxyiminoacetamido]ceph-3-em-4-carboxylic acid, trifluoroacetate salt The product of Stage a) (2.29 g) was dissolved in trifluoroacetic acid (17 ml). After 45 minutes at 21°, the solution was diluted with diisopropyl ether (200 ml) and the precipitate was collected by filtration. The solid was washed with diisopropyl ether and dried to give the title compound (1.40 g). $[\alpha]_D^{21}$ +38.67 (c 0.79, DMSO), $\nu_{max}$ (Nujol) 3700–2200 (NH$_2$, NH, NH$\oplus$ and OH), 177 ($\beta$-lactam), 1718 (acetate) and 1668 and 1540 cm$^{-1}$ (amide).

EXAMPLE 5 a) Diphenylmethyl (6R,7R)-3-Methoxymethyl-7-[(Z)-2-fluoromethoxyimino-2-(2-triphenylmethylaminothiazol-4-yl)acetamido]ceph-3-em-4-carboxylate The title compound (800 mg) was prepared according to the method of Example 3 a) from diphenylmethyl (6R,7R)-7-amino-3-methyoxymethyl ceph-3-em-4-carboxylate, hydrochloride (675) mg and exhibited $[\alpha]_D^{22}$+7.11° (c 0.42, chloroform), $\nu_{max}$ (CHBr$_3$)3380 (NH), 1783 ($\beta$-lactam), 1723 (ester) and 1689 and 1520 cm$^{-1}$ (amide).

b) (6R,7R)-7-[(Z)-2-(2-Aminothiazol-4-yl)-2-fluoromethoxy-imino-acetamido]-3-methoxymethylceph-3-em-4-carboxylic acid The title compound (370 mg) was prepared from the product of Stage a) (730 mg) according to the method of Example 3 b) and exhibited $[\alpha]_D^{22}$+47.2° (c 0.81, DMSO, $\nu_{max}$(pH6 buffer) 227 nm (E$_{1\ cm}^{1\%}$ 359) 252 nm (E$_{cm}^{1\%}$274) $\nu_{infl}$ 296 nm (E$_{1\ cm}^{1\%}$ 111).

EXAMPLE 6 a) Diphenylmethyl (6R,7R)-7-[(Z)-2-fluoromethoxyimino-2-(2-triphenylmethylaminothiazol-4-yl)acetamido]ceph-3-em-4-carboxylate The title compound (2.85 g) was prepared according to the method of Example 3 a) from diphenylmethyl (6R,7R)-7-aminoceph-3-em-4-carboxylate, tosylate salt (2.61 g) and exhibited $[\alpha]_D^{22}$+24.9° (c 0.72, CHCl$_3$), $\nu_{max}$ (CHBr$_3$) 3390 (NH), 1790 ($\beta$-lactam), 1728 (ester) and 1690 and 1520 cm$^{-1}$ (amide).

b) (6R,7R)-7-[(Z)-2-(2-Aminothiazol-4-yl)-2-fluoromethoxyiminoacetamido]-ceph-3-em-4-carboxylate The title compound (1.32 g) was prepared from the product of stage a) (2.73 g) according to the method of Example 3 b) and exhibited $[\alpha]_D^{22}$=86.8° (c 0.62 DMSO), $\lambda_{max}$ (pH6 buffer) 225.5 nm (E$_{1\ cm}^{1\%}$ 430), 298.5 nm (E$_{1\ cm}^{1\%}$ 131), $\lambda_{infl}$ 253 nm (E$_{1\ cm}^{1\%}$ 296).

EXAMPLE 7

(6R,7R)-7-[(Z)-2-(2-Aminothiazol-4-yl-2-fluoromethoxyiminoacetamido]-3-(1-pyridinium methyl) ceph-3-em-4-carboxylate, bis hydrochloride, trihydrate (6R,7R)-7-[(Z)-2-(2-Triphenylmethylaminothiazol-4-yl)-2-fluoromethoxyiminoacetamido]-3-(1-pyridinium-methylceph-3-em-4-carboxylate (7.3 g) was added to formic acid (29 ml) stirred at 20°. After 5 min water (7 ml) was added and the mixture was stirred at 20° C. for a further 2 hr. Dichloromethane (35 ml) was added. The aqueous phase was separated and after the addition of concentrated hydrochloric acid (2 ml) it was extracted with isopropyl ether (2×35 ml). The aqueous solution was diluted with acetone (69 ml) during ca 1.5 hr. The precipitated solid was collected by filtration and washed with acetone/water and then with acetone to give a solid (5 g) after drying it in vacuo.

A 2.50 g aliquot was added to DMF (15 ml) stirred at 20°. The solid dissolved to give a clear solution before crystallization occurred. After 2 hr the solid was collected by filtration, washed successively with DMF and isopropyl ether and dried in vacuo to 2.55 g of crystalline solid. 2.5 g of this solid was added to 0.5 N hydrochloric acid (5 ml) stirred at 20° and when it had dissolved acetone (59 ml) was added during ca 1.5 hr. The solid was collected by filtration, washed with acetone and dried to 1.88 of the title compound.

Water content by Karl Fischer titrimetry: 8.2% m/m. $\nu$max (nujor) includes 3650–2100 (NH, NH, NH$_2$, H$_2$O); 1773 ($\beta$-lactam); 1668+1548 (—CONH) cm$^{-1}$.

(DMSO-d$_6$) include 3.47+3.65 (ABq J=18, 2H); 5.28 (d, J=5, 1H); 5.64+5.90 (ABq, J=12, 2H); 5.78 (J$_{HF}$=48, 2H); 5.89 (1H); 7.05 (1H); 8.24 (t, J=8, 2H); 8.69 (t, J=8, 1H); 9.17 (d, J=6, 2H).

Pharmacy Example
Powder for Injection

| | Per Vial |
|---|---|
| Active substance (as bishydrochloride trihydrate) | 500 mg |
| L-arginine | 177 mg |
| Sodium carbonate, anhydrous | 54 mg |

The components were weighed individually into glass vials. The headspace of each vial was purged with carbon dioxide; then a rubber plug was inserted in the neck and an aluminum overseal applied by crimping. The product was dissolved, as for administration, by the addition of 1.5 ml Water for Injections.

We claim:
1. A compound of the formula (I)

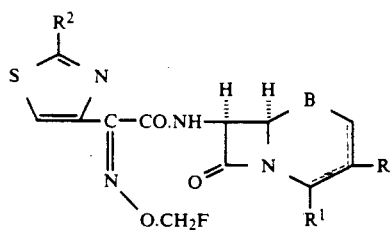

wherein
R[1] is a carboxyl or blocked carboxyl group;
R[2] is an amino or protected amino group;
R is a group of the formula $CH_2OCH_3$;
B is —S— or —SO—(α- or β-); and the dotted line bridging the 2-, 3- and 4-positions indicates that the compound is a ceph-2-em or ceph-3-em compound, and salts thereof.

2. A compound as claimed in claim 1 of the formula (Ia)

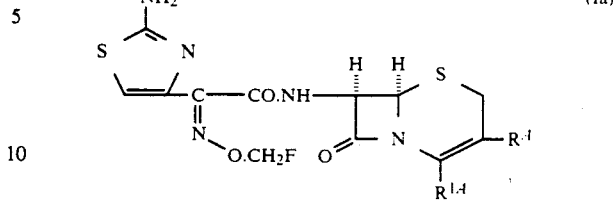

wherein R[4] is a group of the formula $CH_2OCH_3$, and R[14] is a carboxyl group, and the non-toxic salts and non-toxic metabolically labile esters thereof.

3. A pharmaceutical composition comprising ac active ingredient at least one compound of formula (Ia), as defined in claim 2 together with pharmaceutically acceptable carriers and excipients.

* * * * *